United States Patent [19]

Chladek et al.

[11] Patent Number: 5,476,778

[45] Date of Patent: Dec. 19, 1995

[54] METHOD OF GROWING AND ATTENUATING A VIRAL AGENT ASSOCIATED WITH MYSTERY SWINE DISEASE

[75] Inventors: Danny W. Chladek; David E. Gorcyca; Louis L. Harris, all of St. Joseph, Mo.

[73] Assignee: Boehringer Ingelheim Animal Health, Inc., St. Joseph, Mo.

[21] Appl. No.: 207,563

[22] Filed: Mar. 7, 1994

Related U.S. Application Data

[63] Continuation of Ser. No. 71,118, Jun. 1, 1993, abandoned, which is a continuation of Ser. No. 921,891, Aug. 5, 1992, abandoned, which is a continuation-in-part of Ser. No. 841,692, Feb. 26, 1992, abandoned, which is a continuation-in-part of Ser. No. 749,839, Aug. 26, 1991, abandoned.

[51] Int. Cl.6 .............................. C12N 7/00; C12N 7/02; C12N 7/04; C12N 7/08

[52] U.S. Cl. ........................ 435/235.1; 435/236; 435/237; 435/239

[58] Field of Search ..................... 435/237, 236, 435/239, 235.1

[56] References Cited

PUBLICATIONS

Lovia et al. Agri–Practice 12(1):24–34 Jan./Feb. 1991.
Halbur et al.–Viral Pneumonia in Neonatal and Nursey Pigs. Oct. 1992.
Joo et al. Mystery Swine Disease Meeting, Denver, Colo. Livestock Conversation Institute Oct. 6, 1990.
Wensvoort et al. VCT–Quarterly 13(3):121 Jul. 1991.
Pol et al. Vet. Quarterly 13(3):137 Jul. 1991.
Terpstra et al. Vet. Quarterly 13(3):131 Jul. 1991.

*Primary Examiner*—Mary E. Mosher
*Assistant Examiner*—Anthony C. Caputa
*Attorney, Agent, or Firm*—R. P. Raymond; M-E. M. Devlin; A. R. Stempel

[57] ABSTRACT

A viral agent that will mimic "mystery swine" disease has been isolated and described, together with a method of growing the viral agent in vitro, and a method of attenuating the virus for vaccine preparation.

5 Claims, No Drawings

METHOD OF GROWING AND ATTENUATING A VIRAL AGENT ASSOCIATED WITH MYSTERY SWINE DISEASE

This is a continuation of application Ser. No. 08/071,118, filed Jun. 1, 1993, (abandoned) which is a continuation of application Ser. No. 07/921,891, filed Aug. 5, 1992, (abandoned), which is a continuation-in-part of application Ser. No. 07/841,692, filed Feb. 26, 1992, (abandoned), which is a continuation-in-part of application Ser. No. 07/749,839, filed Aug. 26, 1991, (abandoned).

BACKGROUND

Recently, an apparently new swine disease causing heavy losses in breeding herds has appeared in the United States and in certain regions of Canada. Keffaber, K. K., *"Reproducave Failure of Unknown Etiology"*, American Association of Swine Practitioners Newsletter, 1:109 (1989). A similar disease has also been reported in certain regions of Germany, in the Netherlands and also in the United Kingdom and Spain. Wensvoort, G. et al., *"Blue Ear Disease of Pigs"*, Vet. Rec., 128:574 (1991). The most prominent clinical symptom of the disease is the farrowing of dead, or sickly piglets, with some healthy-appearing piglets subsequently faring poorly or developing impaired breathing, CNS symptoms and dying. In some affected herds, up to seventy-five percent of all piglets may be lost. The economic consequences of the disease, accordingly, are devastating. It has been called "mystery swine disease", swine infertility and respiratory syndrome (SIRS), "blue ear disease", and porcine reproductive and respiratory syndrome.

SIRS is an apparently infectious disease, characterized by reproductive failure, respiratory disease and variable clinical signs including anorexia, fever, dyspnea and mild neurological signs. The disease affects all types of swine production facilities, and may be among the most costly of diseases affecting the swine industry today. Polson, D. P. et al. *"Financial Implications of Mystery Swine Disease"*, Proceedings, Livestock Conservation Institute, Denver, Colo. (Oct. 6, 1990).

The infection of sows may go unnoticed, or may manifest itself by impaired general condition lasting one or a few days. For example, the sows may go off feed and show body temperatures above or below normal. In the farrowing phase, the signs of disease include depression, lethargy, pyrexia, occasional vomiting, abortions, stillborns and/or delivery of mummified fetuses. The most frequent clinical sign is the dramatic increase in the number of stillborn pigs. The number of stillbirths can be as high as twenty percent to thirty percent of all births in an infected herd. Many of the fetuses delivered as stillbirths will be macerated, appearing to have been dead for 24 to 48 hours.

As stated above, a major component of SIRS is reproductive failure which manifests itself as premature births, late term abortions, pigs born weak, increased stillbirths, mummified fetuses, decreased farrowing rates and delayed return to estrus. Such clinical symptoms will typically be observed in a herd from 4 to 16 weeks, or even longer. Stillborn fetuses in affected litters often are in the early stages of mummification, as evidenced by tan-brown discoloration of the skin and post-mortem autolysis. Dome-shaped malformation of fetal skulls is sometimes seen.

Clinical signs of respiratory disease are most pronounced in piglets under 3 weeks of age, but are reported to occur in pigs of all ages in infected herds. The diseased piglets grow slowly, have toughened hair coats, respiratory distress ("thumping") and increased mortality (up to about eighty percent pre-weaning mortality).

Findings in preliminary studies of gross and microscopic lesions of SIRS diseased swine suggest that microscopic lung lesions are an important clinical feature of this disease. Despite pronounced respiratory signs, lungs uncomplicated by secondary bacterial infection are either grossly normal or have a mild, diffused tan-gray discoloration of lung surface. Microscopic examination of lung tissue of SIRS-diseased piglets, however, reveals a characteristic pattern of interstitial pneumonitis. Collins, J. E. et al. *"Respiratory Disease in a Swine Herd Experiencing a Reproductive Failure Syndrome"*, Proceedings, Minnesota Swine Conference for Veterinarians, p. 254, St. Paul, Minn. (Sep. 10–18, 1990).

The incidence of SIRS or "mystery swine disease" is widespread in the United States, reported in at least eleven states. The primary causative agents being studied, as reported in the published literature, include encephalomyocarditis virus (EMC), swine influenza virus (SIV), mycotoxins and chlamydia.

THE INVENTION

A tissue homogenate obtained from piglets in SIRS-infected herds consistently reproduced the respiratory and reproductive forms of SIRS when intranasally inoculated in gnotobiotie piglets and pregnant sows. Gnotobiotic piglets so inoculated with either unfiltered or filtered (0.45, 0.22, or 0.1 μm) inoculum became anorectic and developed microscopic lung lesions similar to lesions seen in SIRS-affected herds. The same inoculum also caused reproductive effects identical to those seen in SIRS-infected herds. A viral agent has been recovered from the tissue homogenate. The viral agent will cure a disease that mimics SIRS in piglets and pregnant sows. A deposit of the viral agent has been made on Jul. 18, 1991, with the American Type Culture Collection in Rockville, Md. under the accession number ATCC-VR2332. The vital agent is a fastidious, non-hemagglutinating enveloped RNA virus.

A. ISOLATION

Lung tissue and combined brain-spleen-liver-kidney tissues obtained from an infected piglet in a SIRS-infected herd were homogenized separately. The individual homogenates were mixed with modified Eagle's medium (MEM) containing gentamycin at about 100 μug per mi. Both samples were centrifuged at about 4000×g for about twenty-five minutes. The supernatant was then removed and filtered through a 0.45 micron filter. The tissue and lung homogenate where then combined, and the combined material was used to infect various tissue culture bottles.

Two tests were conducted using 75 cm$^2$ plastic bottles. In Test Number 1, the combined material was inoculated into two bottles of full cell sheet of each of the cell lines listed below. Additionally, to one bottle of each cell line about 2.5 mg of trypsin was added. All other remaining conditions were the same for each bottle of cell line. Serum was not in the culture medium. The inoculum was about 1 ml. All bottles were held for about seven days at approximately 34° C. The results were recorded at the end of about seven days. After freezing and thawing, a sample was taken for a second passage in the same cell line. The remaining material was frozen and stored at about −60° C.

In Test Number 2, the combined material was inoculated into bottles containing the same cell lines as used in Test Number 1. However, the cell sheets were only 20–40% confluent at the time of inoculation. The media contained about 10% fetal calf serum. Again the inoculum was about 1 ml, and the cultures were incubated at about 34° C. for approximately seven days. The results of both Test Number 1 and Test Number 2 are summarized below:

| Cell Line Used | Test Number 1 | Test Number 2 |
| --- | --- | --- |
| Bovine Turbinate (BT) | − | − |
| Feline Kidney (CRFK) | − | − |
| Monkey (Vero) Kidney | − | − |
| Monkey (Vero) Lung | − | − |
| Canine Kidney (MDCK) | − | − |
| Porcine (PK2a) Kidney | − | − |
| Mink Lung | − | − |
| Ferret Lung | − | − |
| Bovine Lung | − | − |
| Buffalo Lung | − | − |
| Bovine Kidney (MDBK) | − | − |
| Swine Testicle (ST) | − | − |
| Monkey Kidney (MA-104) | − | + |
| Human Rectal Tumor (HRT-18) | − | NT |
| Human Lung | NT | − |

+ = CPE Effect
− = No CPE Effect
NT = Not Tested

There was no cytopathic effect observed in Test Number 1 in any of the cell lines evaluated. In Test Number 2, however, small clumps of MA-104 cells began to swell and form "weak holes" in the monolayer around the edges of the bottle. Fluid was separated from the bottle, and passed into a new bottle of MA-104 cells (again 20–40% cell sheet), and then subsequently passed a third time. The cytopathic effect (CPE) became stronger with each passage. The above-described procedures were repeated for the MA-104 cell line employing a full cell sheet. CPE was also observed. Further testing also demonstrated that the viral agent will also grow at about 37° C. The presence of serum may be helpful for the initial isolation of the viral agent. Subsequent passages of the viral agent in the MA-104 cell line will produce the CPE without the presence of serum. However, more pronounced CPE is observed with the use of serum in the growth medium for the MA-104 cell line.

It has also been determined that the viral agent is partially resistant to heating at about 56° C. for approximately 50 minutes. As a result of such heat treatments, the virus titer was reduced by approximately 3 logs. The viral agent has been passed eight times in the MA-104 cell line with good CPE developing in three days at passage five and greater. The titer obtained is approximately 5½ logs ($10^{5.5}$). The viral agent will grow also in additional simian cell lines. Accordingly, it would be within the skill of an individual in the art to grow the SIRS virus ATCC-2332, or mutants thereof, on other cell lines by modification of growing conditions, growth media, etc.

B. IN VIVO TESTING

A third passage harvest was used to inoculate two three-day old gnotobiotic piglets. Both piglets were exposed intranasally, one with 1 ml and the other with 2 ml. The piglets were observed for seven days, and then were euthanized.

Tissue samples were collected for histopathy and for recovery of the viral agent. The histopathology report confirmed that lung lesions in the infected piglets were identical to lung lesions from piglets known to have SIRS. The tissue samples were processed as before, and then cultured on 20–40% and 100% monolayer of the MA-104 cell line with bovine fetal serum. The viral agent was again recovered.

A third passage harvest was also used to inoculate sows in order to verify that the reproductive effects of the disease can be duplicated and confirmed. Two multiparous sows were inoculated intranasally at about ninety-three days of gestation. The sows delivered litters with fifty percent stillborn piglets (8/13 and 6/14 stillborn/live) on days 112 and 114 of gestation, respectively. Seven of the stillborn piglets were partial mummies and the liveborn piglets were weak and failed to nurse vigorously. The viral agent was recovered from tissues of the stillborn piglets.

The viral agent has been recovered from three herds known to have SIRS. Antibody titers to the ATCC-VR2332 agent have been identified in these same herds. Although there are some differences in clinical signs, i.e., cutaneous cyanosis of the ears, tail and udder in European swine, the prevailing opinion is that North American and European diseases are caused by the same virus.

C. VIRAL CHARACTERISTICS

ATCC-VR2332 consistently caused clinical signs and pulmonary lesions in gnotobiotic pigs and negative ImF results, indicating that the virus does not possess a group antigen antigenically similar to viruses in the current genera of the Togaviridae. Thus, the ATCC-VR2332 virus may represent an unidentified genus of the Togaviridae. ATCC-VR2332 virus is also not a known pathogen of swine, because specific antisera to several common viral pathogens of swine failed to either neutralize the virus or detect antigens in infected cells.

ATCC-VR2332 is fastidious non-hemagglutinating enveloped RNA virus. The ATCC-VR2332 virus grows in a continuous cell line, specifically MA-104 and other simian cell lines. The ATCC-VR2332 virus grows to high titers ($10^7$ $TCID_{50}/1$ ml) on the commercial cell line MA-104.

The ATCC-VR2332 virus contains a lipid envelope as indicated by the loss of infectivity following treatment with chloroform. A lipid envelope could also be visualized as an electron translucent ring surrounding the empty particles. The morphology of the SIRS virus is not distinctive on direct electron microscopy (DEM) and would be extremely difficult to identify in preparations containing cellular debris. The ATCC-VR2332 virions could be identified after purification in CsCl gradients, followed by immuno-gold labeling of the virions with anti-ATCC-VR2332 hyperimmune sera and gold conjugate. The buoyant density of the ATCC-VR2332 virions in the CsCl gradients is 1.18–1.19 g/ml. Sucrose gradients consistently resulted in loss of virus titer and were abandoned as a suitable gradient for purification. The morphology of the gradient-purified ATCC-VR2332 particles and the average diameter of 62 nm are very similar to virions of equine Arteritis and lactic dehydrogenase viruses. Equine Arteritis virus has a reported size range of 50–73 nm, similar to the 48–84 nm size for the ATCC-VR2332 virus. 30–35 nm cores in several particles of ATCC-VR2332 were observed, which cores resemble the nucleocapsid cores described for equine Arteritis virus. Thus, morphologically, ATCC-VR2332 most closely resembles the Arteritis virus group.

The presence of an RNA genome of ATCC-VR2332 was confirmed by the ability of this virus to continue to replicate in the presence of 5-bromo-2 deoxyuridine and mitomycin C, which are known to inhibit the replication of DNA and one family of RNA viruses (Retroviridae), but not other RNA viruses. However, the provisional classification of ATCC-VR2332 virus as an RNA virus agrees with the observation that this virus replicates in the cytoplasm of the cell as indicated by the presence of virus antigens detected by ImF. Also, Actinomycin D, which interferes with DNAdependent RNA transcription, has no effect on the replication of the ATCC-VR2332 virus. These results indicate that ATCC-VR2332 virus does not require nuclear functions for replication.

The ATCC-VR2332 virus is heat labile at 37° C. and 56° C., but relatively stable for long periods of time at 4° C. and −70° C. The thermolability of this virus at 37° C. would suggest that the virus is relatively unstable in warm environments. It also has practical applications for propagation of the virus suggesting that growth at temperatures lower than 37° C. will produce higher yields of ATCC-VR2332 virus. Refrigeration should be sufficient for preservation of diagnostic specimens for virus isolation for short periods of time, otherwise the sample should be stored frozen.

In summary, the size, morphology, presence of an RNA genome, and other biologic properties tentatively place ATCC-VR2332 virus in the family Togaviridae. ATCC-VRZ332, however, could not definitely be placed in a known genera of this family. Although, morphologically, ATCC-VR2332 virus closely resembles the arteriviruses, the virus should not be placed in a definite genera until additional information on the RNA and protein structure are available.

D. MODIFIED LIVE VACCINE PREPARATION

A vaccine preparation has been formulated incorporating a modified or attenuated live ATCC-VR2332, which preparation has successfully immunized swine from infection. SIRS virus ATCC-2332 was propagated in the MA-104 continuous cell line. The cell line was grown in flasks containing MEM to which had been added 10% fetal calf serum. The pH of the media was adjusted to 7.2, and incubated at approximately 37° C. The virus was inoculated into the cells by adding about 1 ml of a frozen inoculum to the fluid media. The virus was allowed to absorb onto the cells for 24 hours. At this time, the growth media was changed to a maintenance media which consisted of MEM to which had been added 4% fetal calf serum, pH 7.6. The environment was 35°–37° C. The virus was allowed to grow until 50% of the MA-104 cell sheet was destroyed by the virus. The sample was then frozen down, and prepared for passage onto another flask of MA-104 cells. This process was continued through 25 passages of the virus in the cell line. The virus was then propagated another 12 times at about 31° C. as opposed to 35°–37° C., using the same techniques as described above. The 12th passage was frozen down in small aliquots and designated Master Seed Virus.

EXAMPLE

Preparation of Attenuated ATCC-VR2332

I. Media:
a. Eagles Minimum Essential Medium (MEM) from JRH Biosciences, #200-2041
b. Fetal calf serum from JRH Biosciences
c. Growth media for cell planting–MEM+10% Fetal Calf Serum
d. Maintenance media–MEM 4% Fetal Calf Serum
e. Trypsin-Versene IX
f. Sodium Bicarbonate 5% or saturated II. Tissue Culture:
Cell line used: MA-104 (African Green Monkey Kidney cells kept within 20 passage level (passage 58–78)

III. Equipment:
75 cm tissue culture flasks
Incubator set at 35°–37° C.
Incubator set at 3° C.
Centrifuge IV. Method Used to Attenuate SIRS VR-2332 Virus Grown at 35°–37° C.

A. Preparation of Tissue Culture Stock:
1. 5 to 7 day old MA-104 75cm$^2$ stock bottles are split 1:4 in the following manner:
   a. Pour off all media (50 ml per bottle).
   b. Remove the cell sheet using 10 ml of Trypsin-Versene by incubation at 37° C. for 5–10 minutes.
   c. Remove cells from bottle and centrifuge 270×g for 5–10 minutes.
   d. Decant supernatant and resuspend the cells in 5–10 ml of growth media (MEM 10% FCS).
   e. Put all cells into 200 ml of MEM 10% FCS which is then dispensed into four 75 cm bottles, 50 ml per bottle for a 1:4 split. Bottles are then kept at 35°–37° C. until needed (can be done also without $CO_2$).
   f. 3 or 4 day old bottles which have formed a full cell sheet are now ready for use.
   g. Adjust pH of 50 ml of media in flask to 7.2 pH and then add 1 ml of SIRS virus into media and put flask at 35°–37° C. (can be done also without $CO_2$).
   h. After 24 hours, media is discarded and flask is refed with 50 ml of MEM 4% FCS 7.6 pH and put back at 35°–37° C.
   i. 24 hours after this fluid change, CPE should be showing and, when 50–60% holes are present in cell sheet, freeze down.
   j. Thaw out above bottle and take 1 ml of this fluid and pass into new 75 cm bottle as listed above to make next passage of SIRS VR-2332 virus.

This above procedure was carried out for a total of 25 times or SIRS VR-2332 was passed 25 times, grown at 35°–37° C.

Method Used to Attenuate SIRS VR-2332 Virus Grown at 31° C. (It is important to note that VR-2332 SIRS virus that had been passed 25 time at 35°–37° C. was used to make passage 1 SIRS VR-2332 virus grown at 31° C.)

A. Preparation of Tissue Culture Stock:
1. 5 to 7 day old MA-104 75 cm$^2$ stock bottles are split 1:4 in the following manner:
   a. Pour off all media (50 ml per bottle).
   b. Remove the cell sheet using 10 ml of Trypsin-Versene by incubation at 37° C. for 5–10 minutes.
   c. Remove cells from bottle and centrifuge 270×g for 5–10 minutes.
   d. Decant supernatant and resuspend the cells in 5–10 ml of growth media (MEM 10% FCS).
   e. Put all cells into 200 ml of MEM 10% FCS which is then dispensed into four 75 cm bottles, 50 ml per bottle for 1:4 split. Bottles are then kept at 35°–37° C. until needed (can be done also without $CO_2$).
   f. 3 or 4 day old bottles which have formed a full cell sheet are now ready for use.
   g. Adjust pH of 50 ml of media in flask to 7.2 pH and then add 1 ml of SIRS virus into media and put flask at 31° C. (can be done also without $CO_2$).
   h. After 24 hours, media is discarded and flask is refed with 50 ml of MEM 4% FCS 7.6 pH and put back at 31° C.
   i. 24 hours after this fluid change, CPE should be showing and, when 50–60% holes are present in cell sheet, freeze down.
   j. Thaw out above bottle and take 1 ml of this fluid to make next passage of SIRS VR-2332 virus.

This above procedure was carried out for a total of 12 times at 31° C. The 12th passage of 31° C. grown virus is designated Master Seed Virus for vaccine production.

The cold-adapted virus, Master Seed Virus, titer of approximately $10^{4.5}$ to about $10^{5.0}$ TCID$_{50}$ per milliliter was administered intranasally and intramuscularly to conventional pigs. A pharmaceutical vehicle was administered intranasally and intramuscularly to conventional pigs as a control. The pigs vaccinated with the attenuated virus did not develop any symptoms of SIRS after challenge with ATCCVR-2332 (titer of $10^{4.2}$ TCID$_{50}$ per milliliter), whereas the control pigs did develop symptoms of SIRS. The cold-adapted virus can be put into any compatible, conventional pharmaceutical carrier. Additionally, although the vaccine preparation was administered intranasally and intramuscularly, other routes of administration are possible and envisioned.

As would be apparent to those skilled in the art, various modifications to the growing conditions, method of attenuating the SIRS virus ATCC-VR2332, preparation of vaccine formulations, etc. can be readily made or derived, and all such modifications are envisioned by the inventors hereof.

What is claimed is:

1. A method of growing and isolating swine infertility and respiratory syndrome virus, ATCC-VR2332, which comprises inoculating the virus on a full or partial sheet of simian cells in the presence of serum in a suitable growth medium and incubating the inoculated cell sheet at about 34° C. to 37° C. until CPE is observed.

2. The method as recited in claim 1 wherein the simian cell line is MA-104.

3. A method of attenuating swine infertility and respiratory syndrome virus, ATCC-VR2332, which comprises passaging the virus through a simian cell line on maintenance medium in the presence of serum at pH about 7.6 about twenty-five time at about 35°–37° C. without carbon dioxide, and then passaging the resulting virus through a simian cell line on maintenance medium in the presence of serum at pH about 7.6 about twelve times at about 31° C.

4. The method as recited in claim 3 wherein the simian cell line is MA-104.

5. The method as recited in claim 4 wherein the passages occur without $CO_2$.

* * * * *